United States Patent [19]

King et al.

[11] Patent Number: 5,239,099
[45] Date of Patent: Aug. 24, 1993

[54] AZASILACYCLOALKYL FUNCTIONAL ALKOXYSILANES AND AZASILACYCLOALKYL FUNCTIONAL TETRAMETHYLDISILOXANES

[75] Inventors: Russell K. King; Chi-long Lee, both of Midland, Mich.

[73] Assignee: Dow Corning Corporation, Midland, Mich.

[21] Appl. No.: 940,155

[22] Filed: Sep. 3, 1992

[51] Int. Cl.$^5$ ............................................. C07F 7/10
[52] U.S. Cl. ........................................................ 556/407
[58] Field of Search ........................................... 556/407

[56] References Cited

U.S. PATENT DOCUMENTS

| | | | |
|---|---|---|---|
| 2,823,218 | 2/1958 | Speier et al. | 260/448.2 |
| 3,159,601 | 12/1964 | Ashby | 260/46.5 |
| 3,159,662 | 12/1964 | Ashby | 260/448.2 |
| 3,220,972 | 11/1965 | Lamoreaux | 260/46.5 |
| 3,419,593 | 12/1968 | Willing | 260/448.2 |
| 3,723,497 | 3/1973 | Baney | 260/46.54 A |
| 3,725,449 | 4/1973 | Golitz et al. | 556/407 |
| 3,793,253 | 2/1974 | Quiring et al. | 556/407 X |
| 3,803,194 | 4/1974 | Golitz et al. | 556/607 |
| 4,804,771 | 2/1989 | Pepe | 556/607 |
| 4,888,404 | 12/1989 | Klosowski et al. | 528/15 |
| 5,049,688 | 9/1991 | King et al. | 556/407 |
| 5,110,967 | 8/1992 | King et al. | 556/407 |
| 5,136,064 | 8/1992 | King et al. | 556/407 |

Primary Examiner—Paul F. Shaver
Attorney, Agent, or Firm—Roger H. Borrousch

[57] ABSTRACT

Azasilacycloalkyl functional alkoxysilane which are useful for making polymers for room temperature vulcanizable composition and as adhesion promoters are exemplified by 1-(3-(2,2,4-trimethyl-1-aza-2-silacyclopentyl)propyl)-3-(2-trimethoxysilylethyl)-1,1,3,3-tetramethyldisiloxane and 1-(2-(1,2,4-trimethyl-1-aza-2-silacyclopentyl)ethyl)-3-(2-trimethoxysilylethyl)-1,1,3,3-tetramethyldisiloxane. The methoxy functional azasilacycloalkyl functional compounds can be made from disiloxanes having a silicon-bonded hydrogen atom such as 1-(3-(2,2,4-trimethyl-1-aza-silacyclopentyl)-propyl-1,1,3,3-tetramethyldisiloxane.

13 Claims, No Drawings

AZASILACYCLOALKYL FUNCTIONAL ALKOXYSILANES AND AZASILACYCLOALKYL FUNCTIONAL TETRAMETHYLDISILOXANES

BACKGROUND OF THE INVENTION

1. Field of the Invention

This invention relates to alkoxysilanes which have azasilacycloalkyl functionality.

2. Background Information

A search for new crosslinkers and methods of crosslinking room temperature vulcanizing silicones (RTVs) lead to the discovery of the azasilacyclopentanes of our U.S. Pat. No. 5,136,064, issued Aug. 4, 1992. The olefinic and acetylenic azasilacyclopentanes were found to be useful as silicone RTVs by reacting the aliphatic unsaturation of the azasilacyclopentane with Si—H containing siloxane compounds which would then cure by exposure to moisture or by reaction with siloxane compounds which contained silanol groups. These compositions are described in our U.S. Pat. No. 5,110,967, issued May 5, 1992. These patents are hereby incorporated by reference to show the azasilacyclopentanes and their preparation and their reactions with silicon compounds containing Si—H groups.

The silicone compositions which contain silicon-bonded alkoxy groups and which are RTVs, are desirable products because they produce non-corrosive by-products during curing. However, these compositions exhibit slow cure and low adhesion.

SUMMARY OF THE INVENTION

An object of the present invention is to produce azasilacycloalkyl functional alkoxy silicon compounds. This object is accomplished by this invention.

This invention relates to an azasilacycloalkyl functional alkoxysilane selected from the group consisting of

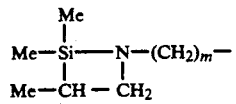  Formula (A)

in which Z is selected from the group consisting of

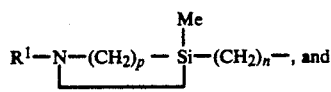  Formula (B)

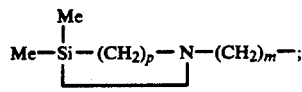  Formula (C)

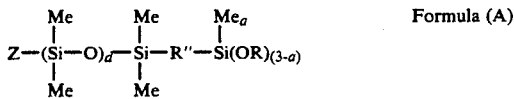  Formula (D)

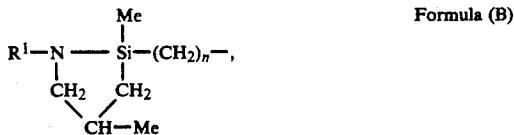  Formula (E)

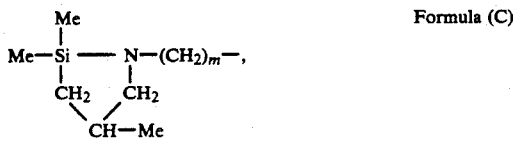  Formula (F)

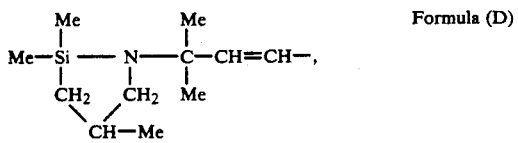  Formula (G)

R is an alkyl radical of from 1 to 3 carbon atoms, Me is methyl, $R^1$ is an alkyl radical having from 1 to 6 inclusive carbon atoms, R" is a divalent hydrocarbon radical selected from the group consisting of —$(CH_2)_b$— and —$CH(Me)(CH_2)_c$—, a is 0 or 1, b is from 2 to 6 inclusive, c is from 0 to 4 inclusive, d has a value of 1 to 3 inclusive, m has a value of 3 to 6 inclusive, n has a value of 2 to 6 inclusive, and p has a value of 4 to 6 inclusive.

DETAILED DESCRIPTION OF THE INVENTION

The azasilacycloalkyl functional alkoxysilanes of this invention are made by reacting an azasilacycloalkane containing aliphatic unsaturation with dimethylsiloxane having silicon-bonded hydrogen atoms at the terminals where the dimethylsiloxane has from 2 to 4 silicon atoms per molecule in the presence of a platinum catalyst which in turn is reacted with an alkoxysilane having aliphatic unsaturation in the presence of a platinum catalyst.

An azasilacyclopentyl functional alkoxysilane of Formula (A) where Z is Formula (C) can be prepared by reacting a dimethylsiloxane having silicon-bonded hydrogen atoms at the terminals where the dimethylsiloxane has 2 to 4 inclusive silicon atoms per molecule, such as 1,1,3,3-tetramethyldisiloxane with 1-allyl-2,2,4-trimethyl-1-aza-2-silacyclopentane in the presence of a platinum catalyst to illustrate this reaction. The resulting product is 1-(3-(2,2,4-trimethyl-1-aza-2-silacyclopentyl)propyl)-1,1,3,3-tetramethyldisiloxane. This reaction is preferably carried out by heating under conditions which prevents the ingress of moisture or water into the reaction mixture. A preferred method is described in Example 1, but, in general, the dimethylsiloxane, a small amount of the azasilacyclopentane, and platinum catalyst are heated and the remainder of the azasilacyclopentane is then slowly added. The amount of the azasilacyclopentane is such that the moles of the dimethylsiloxane exceed the moles of azasilacyclopentane. The product preferably is recovered by distillation. The following equation illustrates the reaction in which 1,1,3,3-tetramethyldisiloxane is used as the dimethylsiloxane having silicon-bonded hydrogen atoms at the terminals

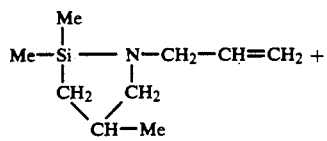

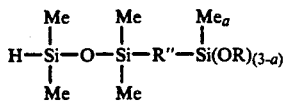

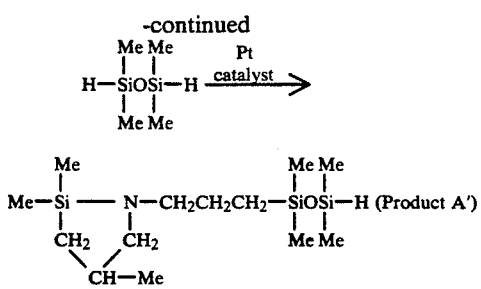

Product A' is 1-(3-(2,2,4-trimethyl-1-aza-2-silacyclopentyl)propyl)-1,1,3,3-tetramethyldisiloxane. Product A' is further reacted with either methylalkenyldialkoxysilane or alkenyltrialkoxysilane to make the azasilacyclopentyl functional alkoxysilane Formula (A). Examples of methylalkenyldialkoxysilane include methylvinyldimethoxysilane, methylvinyldiethoxysilane, methylvinyldipropoxysilane, methylvinyldiisopropoxysilane, methylallyldimethoxysilane, methylallyldiethoxysilane, methyl-allyldipropoxysilane, methylbuten-1-yldi-methoxysilane, methylpenten-1-yldimethoxysilane, methylpenten-1-yldiethoxy-silane, methylhexen-1-yldimethoxysilane, and methyl-hexen-1-yldiethoxysilane. Examples of alkenyltrialkoxysilane include vinyltrimethoxysilane, vinyltriethoxysilane, vinyltripropoxysilane, allyltrimethoxysilane, allyltriethoxysilane, allyltripropoxysilane, buten-1-yltrimethoxysilane, buten-1-yltriethoxysilane, buten-1-yltripropoxysilane, penten-1-yltrimethoxysilane, penten-1-yltriethoxysilane, penten-1-yltripropoxysilane, hexen-1-yltrimethoxysilane, and hexen-1-yltriethoxysilane. Product A' is combined with an alkoxysilane in the presence of platinum catalyst and preferably heated to cause the alkenyl group of the alkoxysilane to add across the Si—H group of Product A'. This reaction is illustrated by the following equation:

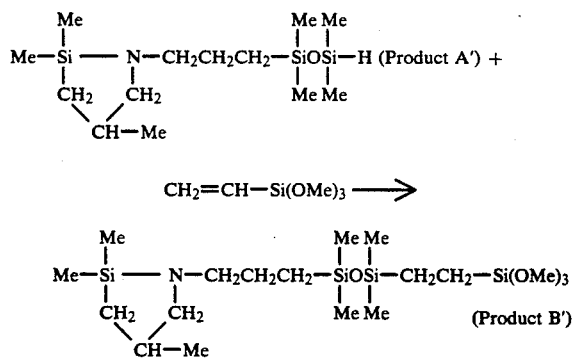

Product B' is 1-(3-(2,2,4-trimethyl-1-aza-2-silacyclopentyl)propyl)-3-(2-trimethoxysilylethyl)-1,1,3,3-tetramethyldisiloxane. Product B' can be further purified by distillation of the reaction product under reduced pressure.

Other azasilacyclopentyl functional alkoxysilanes in which m is 4, 5, or 6, can be prepared in the same manner by substituting for the 1-allyl-2,2,4-trimethyl-1-aza-2-silacyclopentane, 1-(buten-1-yl)-2,2,4-trimethyl-1-aza-2-silacyclopentane, 1-(penten-1-yl)-2,2,4-trimethyl-1-aza-2-silacyclopentane, or 1-(hexen-1-yl)-2,2,4-trimethyl-1-aza-2-silacyclopentane.

An azasilacyclopentyl functional alkoxysilane of Formula (A) where Z is Formula (B) can be prepared by reacting a dimethylsiloxane having a silicon-bonded hydrogen atom at one terminal and a trimethoxysilylalkyl at the other terminal and having a formula

in which R, R", and a are defined above with 1,2,4-trimethyl-2-alkyl-1-aza-2-silacyclopentane in the presence of a platinum catalyst. These azasilacyclopentyl functional alkoxysilanes of Formula (A) where Z is Formula (B) can be illustrated by the reaction of 1-(2-trimethoxysilylalkyl)-1,1,3,3-tetramethyldisiloxane; 1-(1-trimethoxysilylalkyl)-1,1,3,3-tetramethyldisiloxane; or a mixture of these with 1,2,4-trimethyl-2-vinyl-1-aza-2-silacyclopentane in the presence of a platinum catalyst. This reaction is preferably carried out by heating under conditions which prevent the ingress of moisture or water into the reaction mixture. A preferred method is described in Example 2. These siloxanes can be prepared by reacting R'Me$_a$Si(OR)$_{(3-a)}$ in which R' is an alken-1-yl radical having from 2 to 6 carbon atoms with $$H(Me_2SiO)_dSiMe_2H$$

in which d is defined above, in the presence of a platinum catalyst. The alken-1-yl alkoxysilanes are illustrated above. The method for preparing these siloxanes are further described by Klosowski et al in U.S. Pat. No. 4,888,404, issued Dec. 19, 1989, which is hereby incorporated by reference to show examples of such siloxanes and their preparation. The product is preferably recovered by distillation. The following equation illustrates the reaction

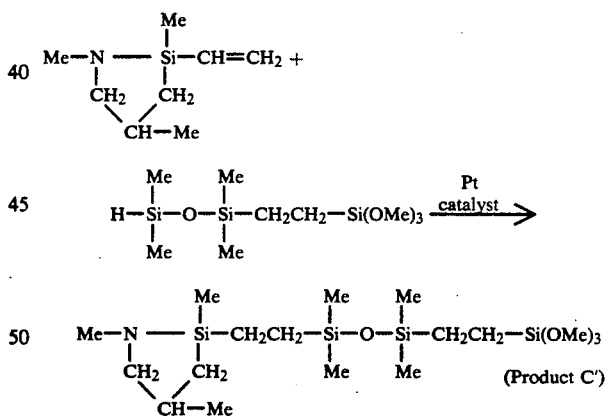

Product C' is 1-(2-(1,2,4-trimethyl-1-aza-2-silacyclopentyl)ethyl)-3-(2-trimethoxysilylethyl)-1,1,3,3-tetramethyldisiloxane. The reaction product which contains Product C' can be further purified by distillation at reduced pressure. In the above reaction, the Me (methyl radical) on the ring nitrogen atom is used for illustrative purposes as an example of R$^1$ which can be an alkyl radical selected from the methyl, ethyl, propyl, butyl, pentyl, and hexyl. In the reactions which follow, in each case, where a methyl is shown on the ring nitrogen atom, it is used as the preferred alkyl radical for R$^1$.

The aliphatic unsaturated azasilacyclopentanes used to make the azasilacyclopentyl functional alkoxysilanes of the present invention have the general formulae

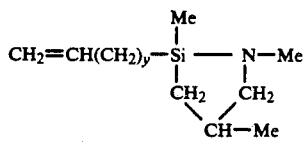

and

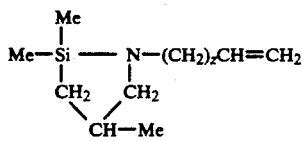

in which y has a value of from 0 to 4 inclusive; z has a value of from 1 to 4 inclusive; and Me is methyl radical. These azasilacyclopentanes are described in our U.S. Pat. No. 5,136,064, which is incorporated by reference to show these azasilacyclopentanes and their preparation.

An azasilacyclopentyl functional alkoxysilanes of Formula (A) where Z is Formula (D) can be made by the same method as the preparation for the azasilacyclopentyl functional alkoxysilanes of Formula (A) where Z is Formula (C). In these preparations, the aliphatic unsaturated azasilacycloalkane has the formula

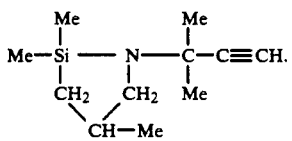

This azasilacycloalkane can be prepared by the method described in U.S. Pat. No. 5,136,064, where the reaction for the preparation is

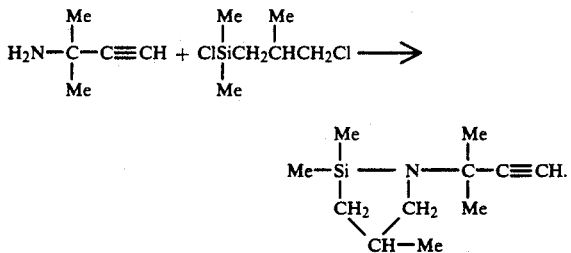

An azasilacyclobutyl functional alkoxysilane of Formula (A) where Z is Formula (E) can be prepared by reacting a dimethylsiloxane having silicon-bonded hydrogen atoms at the terminals of the formula

in which d is defined above, with an azasilacyclobutane of the formula

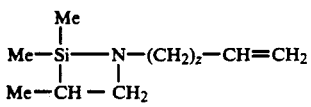

where z has a value of 1 to 4 inclusive. This reaction is done in the presence of a platinum catalyst and the following equation illustrates such a reaction

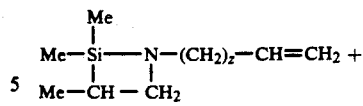

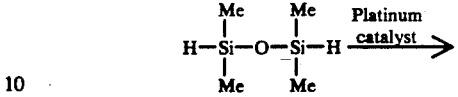

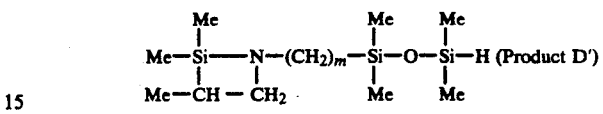

Product D' is further reacted with either methylalkenyldialkoxysilane or alkenyltrialkoxysilane to make the azasilacyclobutyl functional alkoxysilane Formula (A) where Z is Formula (E). Examples of other alkoxysilanes which can be used are described above. Product D' is combined with an alkoxysilane in the presence of platinum catalyst and preferably heated to cause the alkenyl group of the alkoxysilane to add across the Si-H group of Product D'. This reaction is illustrated by the following equation:

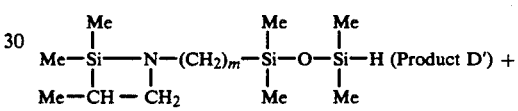

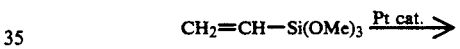

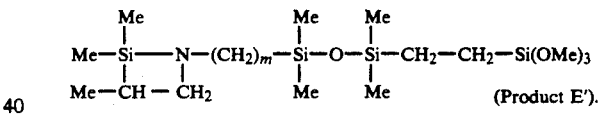

The preparation of azasilacyclobutanes can be illustrated by the following: Diallylamine was reacted with chlorodimethylsilane in heptane in the presence of triethylamine to give diallylaminodimethylsilane as shown by the following equation

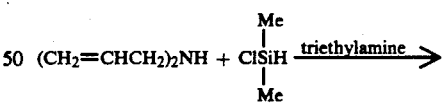

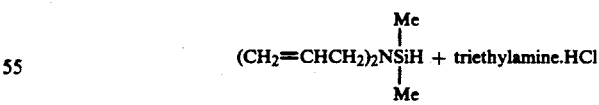

The silane product was obtained by ambient pressure distillation after removal of triethylamine hydrochloride by filtration. 1-allyl-2,2,3-trimethyl-1-aza-2-silacyclobutane was made by intramolecular hydrosilation of the diallyldimethylsilane. This reaction was carried out at 80° C. in the presence of $PtCl_2(PPh_3)_2$ in benzene. The starting material was consumed in four hours to give a product mixture of 83 mole percent of the azasilacyclobutane and 17 mole percent of azasilacyclopentane as illustrated by the following equation

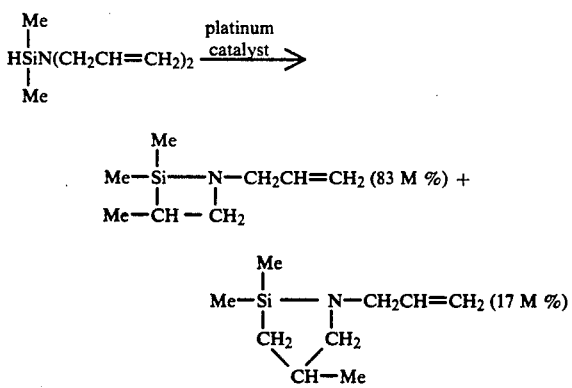

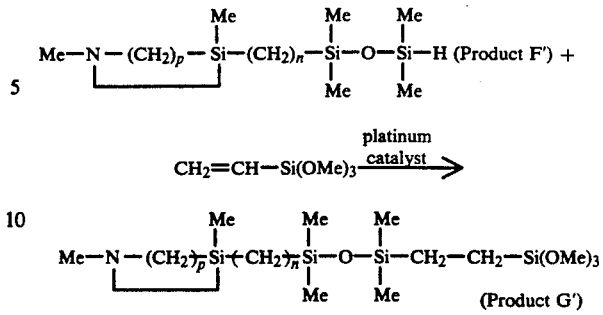

Total yield of product was 77 weight percent. The azasilacyclobutane can be reacted with 1,1,3,3-tetramethyldisiloxane in the presence of a platinum catalyst which in turn can be reacted with an alkoxysilane having aliphatic unsaturation as described above to make an azasilacyclobutyl functional alkoxysilane of Formula (A).

An azasilacycloalkyl functional alkoxysilane of Formula (A) where Z is Formula (F) can be prepared by reacting a dimethylsiloxane having silicon-bonded hydrogen atoms at the terminals of the formula

in which d is defined above, with an azasilacycloalkane of the formula

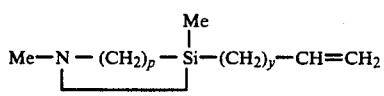

where y has a value of 0 to 4 inclusive and p has a value of 4 to 6 inclusive. This reaction is done in the presence of a platinum catalyst and the following equation illustrates such a reaction

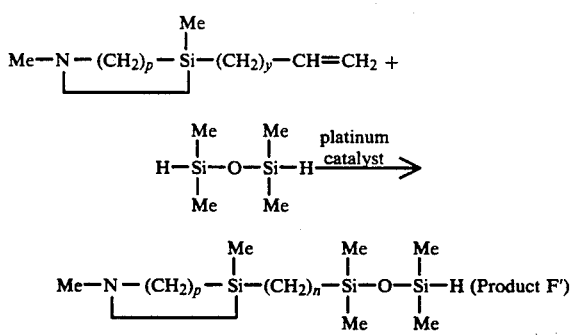

where n has a value of 2 to 6 inclusive.

Product F' is further reacted with either methylalkenyldialkoxysilane or alkenyltrialkoxysilane to make the azasilacycloalkyl functional alkoxysilane Formula (A) where Z is Formula (F). Examples of other alkoxysilanes which can be used are described above. Product F' is combined with an alkoxysilane in the presence of platinum catalyst and preferably heated to cause the alkenyl group of the alkoxysilane to add across the Si-H group of Product F'. This reaction is illustrated by the following equation:

An azasilacycloalkane used to provide the functionality of Formula (F), 2-vinyl-1,2-dimethyl-1-aza-2-silacycloalkane, can be made by reacting

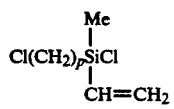

with methylamine using the procedure described in U.S. Pat. No. 3,146,250, issued Aug. 25, 1964, to Speier which is hereby incorporated by reference to show a method of preparation for azasilacycloalkanes. The chlorosilane of the formula

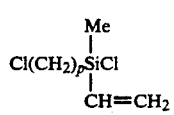

can be made by reacting

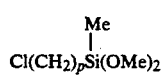

with vinyl magnesium bromide, followed by reaction with acetyl chloride in the presence of ferric trichloride catalyst. The methoxysilane of the formula

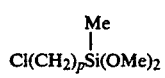

can be made by reacting

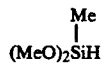

with $CH_2=CH-(CH_2)_{(p-2)}Cl$ in the presence of a platinum catalyst. Other reactions are describe in an article by Speier et al, in the Journal of Organic Chemistry, vol. 36, pages 3120–3126, (1971), entitled "Syntheses of (3-Aminoalkyl)silicon Compounds."

An azasilacycloalkyl functional alkoxysilane of Formula (A) where Z is Formula (G), 1-allyl-2,2-dimethyl-1-aza-2-silacycloalkane, can be prepared by reacting a dimethylsiloxane having silicon-bonded hydrogen atoms at the terminals of the formula

in which d is defined above, with an azasilacycloalkane of the formula

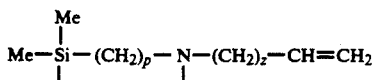

where z has a value of 1 to 4 inclusive and p has a value of 4 to 6 inclusive. This reaction is done in the presence of a platinum catalyst and the following equation illustrates such a reaction

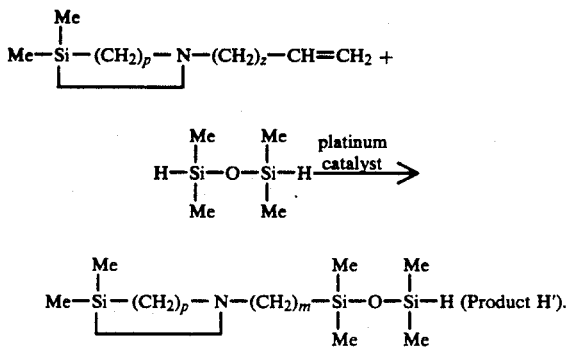

where m has a value of 3 to 6 inclusive.

Product H' is further reacted with either methylalkenyldialkoxysilane or alkenyltrialkoxysilane to make the azasilacycloalkyl functional alkoxysilane Formula (A) where Z is Formula (G). Examples of other alkoxysilanes which can be used are described above. Product H' is combined with an alkoxysilane in the presence of platinum catalyst and preferably heated to cause the alkenyl group of the alkoxysilane to add across the Si—H group of Product H'. This reaction is illustrated by the following equation:

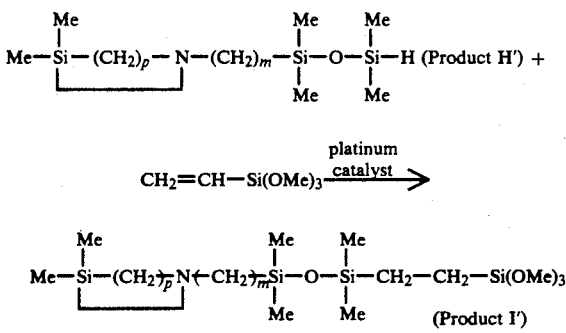

The 1-allyl-2,2-dimethyl-1-aza-2-silacycloalkanes can be made by reacting

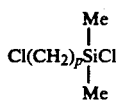

with $CH_2=CHCH_2NH_2$ using a procedure described in U.S. Pat. No. 3,146,250. The chlorosilane of the formula

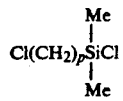

can be made by reacting

with $CH_2=CH(CH_2)_{(p-2)}Cl$ in the presence of a platinum catalyst.

The olefinic unsaturation of the azasilacycloalkane reacts with the Si—H group of the tetramethyldisiloxane in the presence of a platinum catalyst. The reaction resulting from this combination is termed an "addition reaction" or a "hydrosilylation reaction" where the olefinic bond reacts with the silicon-bonded hydrogen such that the Si—H adds across the double bond. Platinum catalysts are well known in the art for catalyzing this reaction. These platinum catalysts include the chloroplatinic acid described by Speier et al in U.S. Pat. No. 2,823,218, issued Feb. 11, 1958; complexes of chloroplatinic acid with low molecular weight vinyl-containing polydiorganosiloxanes such as syn-divinyltetramethyldisiloxane as described by Willing in U.S. Pat. No. 3,419,593, issued Dec. 31, 1968; alkene complexes described by Ashby in U.S. Pat. No. 3,159,601, issued Dec. 1, 1964, and U.S. Pat. No. 3,159,662, issued Dec. 1, 1964; the platinum acetylacetonate described by Baney in U.S. Pat. No. 3,723,497, issued Mar. 27, 1973; the platinum alcoholates described by Lamoreaux in U.S. Pat. No. 3,220,972, issued Nov. 30, 1965; and in many more patents which describe various types of platinum catalysts. These patents describing platinum catalysts are hereby incorporated by reference to show the platinum catalysts and to show the hydrosilylation reaction.

The azasilacycloalkyl functional alkoxysilanes of the present invention can be used as adhesion promoters in RTV compositions and as precursors for preparing polymers useful for making RTV compositions.

The following syntheses and examples are presented for illustrative purposes and should not be construed as limiting the invention which is delineated in the claims. In the following examples, "part" and "parts" are respectively "part by weight" and "parts by weight", and Me=methyl.

SYNTHESIS 1

Preparation of
2,2,4-trimethyl-1-allyl-1-aza-2-silacyclopentane

The 2,2,4-trimethyl-1-allyl-1-aza-2-silacyclopentane was prepared as follows. Chlorodimethyl(3-chloro-2-methylpropyl)silane (100 g, 0.54 mol) was slowly added to 211.73 g (3.71 mol, 6.87 eq) of undistilled allyl amine resulting in an exothermic reaction. This reaction mixture was stirred at room temperature for 15 hours, heated to reflux at atmospheric pressure for 72 hours, and heated to 120° C. under about 50 psig pressure for 16 hours. The following GC-MS ratios shown in the Table exemplified the reactions progression and the spectra observed were as shown.

| RETENTION TIME, MIN | 15 HOURS 20° C. | 24 HOURS REFLUX | 72 HOURS REFLUX | 16 HOURS 120° C. | COMPOUND |
| --- | --- | --- | --- | --- | --- |
| 2.70 | 0.0 | 3.9 | 21.3 | 71.9 | E |
| 2.82 | 0.0 | 1.0 | 1.1 | 0.9 | F |
| 3.20 | 50.4 | 11.0 | 4.1 | 0.0 | G |
| 5.19 | 29.5 | 63.0 | 40.2 | 0.0 | H |
| 8.46 | 20.0 | 8.8 | 8.1 | 2.4 | I |
| 9.58 | 0.0 | 9.3 | 10.1 | 6.1 | J |
| 10.58 | 0.0 | 3.1 | 15.1 | 18.7 | K |

Compound E was 2,2,4-trimethyl-1-allyl-1-aza-2-silacyclopentane and the spectra was 169 (819), M+; 154 (1326), M+—$CH_3$; 142 (1074), M+—Vi; 127 (375), M+—$C_3H_6$; 126 (354), M+—$C_3H_7$; 100 (784), M-69; 86 (8734), $Me_2SiN=CH_2$+; 59 (10000), $Me_2SiH$+. Compound F was not determined.

Compound G was chlorodimethyl(3-chloro-2-methylpropyl)silane and the spectra was 184 (0), M+; 169 (233), M+—Me; 137 (292), M+—47; 113 and 115 (2459 and 1991), $Cl_2MeSi$+; 93 (9786), $ClMe_2Si$+; 56 (10000), $C_4H_8$.

Compound H was allylaminodimethyl(3-chloro-2-methylpropyl)silane and the spectra was 205 (10), M+; 190 (79), M+—Me; 170 (153), M+—Cl; 149 (618), M+—$C_4H_8$; 134 and 136 (1263 and 508), M+—$CH_3$—$C_4H_8$; 120 and 122 (1250 and 625), unassigned; 114 (10000), $CH_2=CHCH_2NHSiMe_2$+; 98 (4709), unassigned; 93 and 95 (4999 and 1948), $ClMe_2Si$+.

Compound I was 1,1,3,3-tetramethyl-1,3-bis(3-chloro-2-methylpropyl)disiloxane and the spectra was 314 (0), M+; 187 and 189 (2045 and 1291), $ClMe_2Si$-$OSiMeCl$+; 167 and 169 (10000 and 3897), $ClMe_2Si$-$OSiMe_2$+.

Compound J was 1,1,3,3-tetramethyl-1-(3-chloro-2-methylpropyl)-1-(3-allylamino-2-methylpropyl)disiloxane and the spectra was 335 (0), M+; 320 (52), M+—Me; 167 and 169 (1216 and 463), $ClMe_2Si$-$OSiMe_2$+; 70 (10000), $CH_2=CHCH_2NH=CH_2$+.

Compound K was 1,1,3,3-tetramethyl-1,3-bis(3-allylamino-2-methylpropyl)disiloxane and the spectra was 356 (0), M+; 170 (1017), $CH_2=CHCH_2NHCH_2CH(CH_3)CH_2SiMe_2$+; 169 (1177), peak 170-H; 70 (10000), $CH_2=CHCH_2NH=CH_2$+.

Upon cooling the product of the reaction, a two phase system resulted. The upper phase weighed 111.85 g and contained most of the product 2,2,4-trimethyl-1-allyl-1-aza-2-silacyclopentane. The lower phase weighed 177.12 g and was an amber viscous liquid. This lower phase was concentrated at atmospheric pressure with a pot temperature of 120° C. to 122 g. Another 4.0 g of the upper phase was separated upon cooling. The combined product phases were distilled under vacuum. After a slow evolution of allylamine, the product codistilled with an ammonium salt at 78° C. and 30 mmHg. Filtration gave 51.63 g (56% yield) of essentially pure 2,2,4-trimethyl-1-allyl-1-aza-2-silacyclopentane. The $^{13}C$ NMR was: 138.13, vinyl; 114.39, vinyl; 58.98, allyl $CH_2$; 50.31, ring $CH_2N$; 31.88, CH; 21.94 and 21.50, $SiCH_2$ and C-Me; 0.22 and −0.76, SiMe. The $^{29}Si$ NMR spectra had one peak at 15.56 ppm relative to tetramethylsilane.

SYNTHESIS 2

Preparation of 1,2,4-Trimethyl-2-vinyl-1-aza-2-silacyclopentane

The 1,2,4-trimethyl-2-vinyl-1-aza-2-silacyclopentane was prepared as follows. To a solution of 50.0 g (254 mmol) of dimethoxy-methyl(3-chloro-2-methylpropyl)-silane in 250 ml of diethyl ether in a three-necked, 1 L (liter) round-bottom flask fitted with a mechanical stirrer, nitrogen inlet, and addition funnel was added over a one hour, a solution of 290 ml (290 mmol) of 1M (molar) vinyl magnesium bromide in tetrahydrofuran (THF). The reaction mixture was allowed to stir overnight under a nitrogen atmosphere at room temperature and the slightly yellowish liquid was decanted from the solids. The solvents were removed at 40° C. and 9 mmHg to yield 68.09 g of a yellow liquid with considerable amounts of solids. To this was added 50 ml of benzene and the salts were removed by filtration through a course glass frit funnel. The collected solids were washed with two 30 ml portions of benzene. The combined organic fractions were stripped at 50° C. and 9 mmHg to yield 40.19 g of liquid with a small amount of salts. The results of gas chromatography-mass spectroscopy (GC-MS) showed the following composition of the liquid:

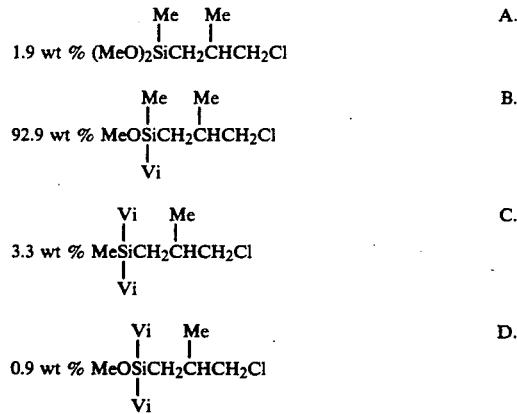

3.1 wt % of 9 unidentified impurities at an order of magnitude lower level.

The mass spectra was used to identify these compounds and the results were:

For B compound: 192, not observed, M+; 165(10), M—Vi; 137 (10),NA; 121(210), (MeO)ViClSi+; 109(230), (MeO)MeClSi+; 101(780), (MeO)MeViSi+; 56(1000), $C_4H_8$+ where data are presented as charge (m/e), (relative intensity).

For C compound: 188, not observed, M+; 161(8), M—Vi; 117 (280), $Vi_2ClSi$+; 105(284), MeViSi+; 97(489), $Vi_2MeSi$+; 56(1000), $C_4H_8$+.

For D compound: 204, not observed, M+; 177(10), M—Vi; 121 (290), (MeO)ViClSi+; 113(620), (MeO)-Vi₂Si+; 56(1000), C₄H₈+.

The $^{29}Si$ nuclear magnetic resonance(NMR) had one major peak at 6.63 ppm relative to tetramethylsilane. The crude product was purified by short path distillation. The fraction boiling at 75° C. at 6 mmHg weighed 28.22 g (58% yield) and was identified as compound B, methoxymethylvinyl(3-chloro-2-methylpropyl)silane.

Chloromethylvinyl(3-chloro-2-methylpropyl)silane was prepared as follows. A mixture of 28.00 g (143.3 mmol) of compound B in 15.5 ml (17.10 g, 217.9 mmol, 1.5 eq) of acetyl chloride was allowed to sit at ambient temperature for 12 hours. A slight exotherm was noted. The low boiling material was removed by distillation and the product distilled at 88° C. to 90.5° C. and 30 mmHg to give 25.2 g of material (88% yield). The product was chloromethylvinyl(3-chloro-2-methylpropyl)silane as was identified by $^{13}C$ NMR: 134.79 and 134.73 and 134.68 (1:2:1, 1.67), SiVi; 52.93 (1.00), CH₂Cl; 31.51 and 31.48 (0.83), CH; 22.88 and 22.84 (0.97), CHMe; 20.13 and 20.10 (1.01), SiCH₂; 0.59 and 0.54 (0.68), SiMe and by $^{29}Si$ NMR: 17.81 and 17.78 (1:1) where data are presented as ppm (relative intensity).

Methylamine was condensed into a 1 L round-bottom flask and distilled from sodium. To 490 ml (340 g, 11 mol) of methylamine was slowly added 309.8 g (1.57 mol) of chloromethylvinyl(3-chloro-2-methylpropyl)silane, which resulted in two phases. The two phase system was transferred to a Parr reactor and heated at 110° C. and 230 psig for 10 hours. The reaction mixture was cooled to −10° C., transferred to a 2 L round-bottom flask and 400 ml of cold pentane was added. The layers were separated, and the upper organic phase concentrated. After concentration, some ammonium slats had precipitated. These salts were removed by filtration and the product purified by distillation at reduced pressure to yield about 160 g (60% yield) of aza-silacyclopentane with a small amount of ammonium salts. The distilled product was 97% pure 1,2,4-trimethyl-2-vinyl-1-aza-2-silacyclopentane with two major higher boiling impurities (about 1 wt % each) and numerous minor higher boiling impurities. The GC-MS data was: 1,2,4-Trimethyl-2-vinyl-1-aza-2-silacyclopentane, Retention Time 2.00 min; 155 (365), M+; 154 (243), M+—H; 140(97), M+—Me; 126 (113), M+—Vi; 113 (962), M+—C₃H₇; 112 (1000), M+—C₃H₇; 89 (396), MeViSiN=CH₂+; 71 (465) MeViSiH+. The $^{13}C$ NMR spectra was: 138.23 and 137.98, terminal vinyl; 132.86 and 137.98, internal vinyl; 62.19 and 61.92, N—CH₂; 33.93 and 33.80, methine; 32.09 and 32.06, NMe; 21.48 and 21.54, CHMe; 21.23 and 20.95 Si—CH₂; −3.43 and −4.29, SiMe. The $^{29}Si$ NMR had peaks at 6.229 and 6.039 relative to tetramethylsilane.

EXAMPLE 1

Synthesis of 1-(3-(2,2,4-trimethyl-1-aza-2-silacyclopentyl)propyl-1,1,3,3-tetramethyldisiloxane To 169 g (1.26 mol) of 1,1,3,3-tetramethyldisiloxane, 0.25 g of a chloroplatinic acid-1,3-divinyl-1,1,3,3-tetramethyldisiloxane complex having about 0.7 weight percent platinum, and 17 g of 1-allyl-2,2,4-trimethyl-1-aza-2-silacyclopentane as prepared by Synthesis 1, at 80° C., in a 500 ml round-bottom flask fitted with a magnetic stirrer, condenser, and addition funnel, 153.44 g (1.01 mol) of 1-allyl-2,2,4-trimethyl-1-aza-2-silacyclopentane was slowly added over a 35 minute period. The resulting reaction mixture was allowed to stir at 80° C. overnight and the product was isolated by distillation at reduced pressure. The portion boiling between 78° C. and 82° C. at 0.1 mm Hg weighed 181 g and was identified as 1-(3-(2,2,4-trimethyl-1-aza-2-silacyclopentyl)propyl-1,1,3,3-tetramethyldisiloxane. Synthesis of 1-(3-(2,2,4-trimethyl-1-aza-2-silacyclopentyl)propyl)-3-(2-trimethoxysilylethyl)-1,1,3,3-tetramethyldisiloxane A mixture of the 20.67 g (68.1 mmol) of 1-(3-(2,2,4-trimethyl-1-aza-2-silacyclopentyl)propyl-1,1,3,3-tetramethyldisiloxane, 10.6 g (71.5 mmol) of vinyltrimethoxysilane which had been distilled from sodium, and 0.03 g of a chloroplatinic acid1,3-divinyl-1,1,3,3-tetramethyldisiloxane complex having about 0.7 weight percent platinum was heated for one hour at 120° C. The resulting product was distilled and the distillate was collected at 152° C. and 0.1 mm Hg. The amount of distillate collected was 28.2 g of 1-(3-(2,2,4-trimethyl-1-aza-2-silacyclopentyl)propyl)-3-(2-trimethoxysilylethyl)-1,1,3,3-tetramethyldisiloxane which was identified by $^{13}C$ and $^{29}Si$ NMR (nuclear magnetic resonance) and GC-MS.

EXAMPLE 2

Synthesis of 1-(2-(1,2,4-trimethyl-1-aza-2-silacyclopentyl)ethyl)-3-(2-trimethoxysilylethyl)-1,1,3,3-tetramethyldisiloxane and 1-(2-(1,2,4-trimethyl-1-aza-2-silacyclopentyl)ethyl)-3-(1-trimethoxy-silylethyl)-1,1,3,3-tetramethyldisiloxane To 59.2 g of a 2:1 mole ratio of 1-(2-trimethoxysilylethyl)-1,1,3,3-tetramethyldisiloxane and 1-(1-trimethoxysilylethyl)-1,1,3,3-tetramethyldisiloxane and 32.8 g of 1,2,4-trimethyl-2-vinyl-1-aza-2-silacyclopentane as prepared by Synthesis 2 was added 0.07 g a chloroplatinic acid-1,3-divinyl-1,1,3,3-tetramethyldisiloxane complex having about 0.7 weight percent platinum. The resulting mixture was then heated for 2 hours at 160° C. and then distilled collecting the distillate coming off at 115° C. to 125° C. and 0.1 mm Hg. The amount of distillate collected was 86.0 g and was identified by $^{13}C$ and $^{29}Si$ NMR and GC-MS to be a mixture of 1-(2-(1,2,4-trimethyl-1-aza-2-silacyclo-pentyl)ethyl)-3-(2-trimethoxysilylethyl)-1,1,3,3-tetramethyldisiloxane and 1-(2-(1,2,4-trimethyl-1-aza-2-silacyclopentyl)ethyl)-3-(1-trimethoxy-silylethyl)-1,1,3,3-tetramethyldisiloxane.

That which is claimed is:

1. An azasilacycloalkyl functional alkoxysilane selected from the group consisting of

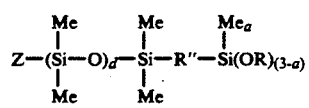

in which Z is selected from the group consisting of

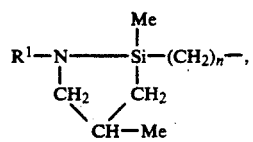

-continued

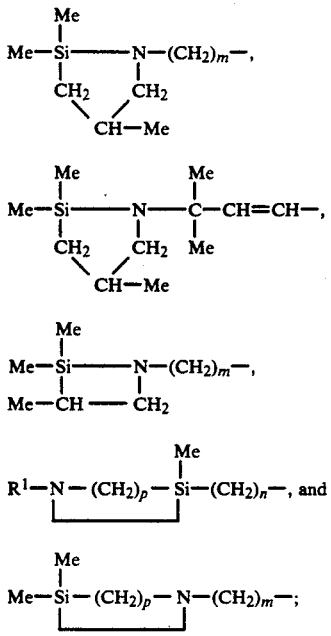

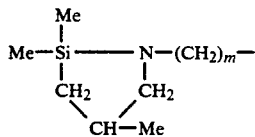

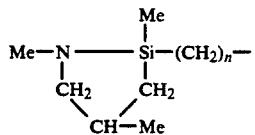

R is an alkyl radical of from 1 to 3 carbon atoms, Me is methyl, $R^1$ is an alkyl radical having from 1 to 6 inclusive carbon atoms, R" is a divalent hydrocarbon radical selected from the group consisting of —$(CH_2)_b$— and —$CH(Me)(CH_2)_c$—, a is 0 or 1, b is from 2 to 6 inclusive, c is from 0 to 4 inclusive, d has a value of 1 to 3 inclusive, m has a value of 3 to 6 inclusive, n has a value of 2 to 6 inclusive, and p has a value of 4 to 6 inclusive.

2. The azasilacycloalkyl functional alkoxysilane in accordance with claim 1 in which $R^1$ is methyl.

3. The azasilacycloalkyl functional alkoxysilane in accordance with claim 2 in which Z is an azasilacyclopentyl group of the formula

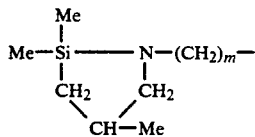

and d is 1.

4. The azasilacycloalkyl functional alkoxysilane in accordance with claim 2 in which Z is an azasilacyclopentyl group of the formula

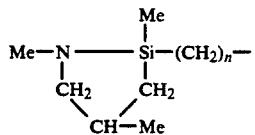

and d is 1.

5. The azasilacyclopentyl functional alkoxysilane of claim 3 which is 1-(3-(2,2,4-trimethyl-1-aza-2-silacyclopentyl)propyl)-3-(2-trimethoxysilylethyl)-1,1,3,3-tetramethyldisiloxane.

6. The azasilacyclopentyl functional alkoxysilane of claim 4 which is 1-(2-(1,2,4-trimethyl-1-aza-2-silacyclopentyl)ethyl)-3-(2-trimethoxysilylethyl)-1,1,3,3-tetramethyldisiloxane.

7. The azasilacyclopentyl functional alkoxysilane of claim 4 which is 1-(2-(1,2,4-trimethyl-1-aza-2-silacyclopentyl)ethyl)-3-(1-trimethoxysilylethyl)-1,1,3,3-tetramethyldi-siloxane.

8. The azasilacyclopentyl functional alkoxysilane of claim 4 which is a mixture of 1-(2-(1,2,4-trimethyl-1-aza-2-silacyclopentyl)ethyl)-3-(2-trimethoxysilylethyl)-1,1,3,3-tetramethyldisiloxane and 1-(2-(1,2,4-trimethyl-1-aza-2-silacyclopentyl)ethyl)-3-(1-trimethoxysilylethyl)-1,1,3,3-tetramethyldisiloxane.

9. An azasilacyclopentyl functional tetramethyldisiloxane of the formula

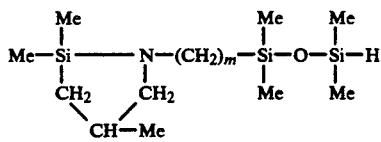

in which Me is methyl, and m has a value of 3 to 6 inclusive.

10. An azasilacyclopentyl functional tetramethyldisiloxane of the formula

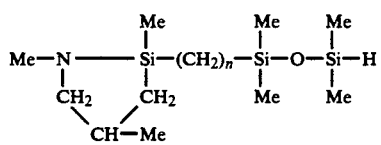

in which Me is methyl and n has a value of 2 to 6 inclusive.

11. An azasilacyclobutyl functional tetramethyldisiloxane of the formula

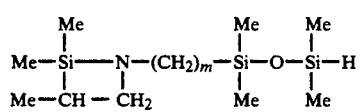

in which Me is methyl, and m has a value of 3 to 6 inclusive.

12. An azasilacycloalkyl functional tetramethyldisiloxane of the formula

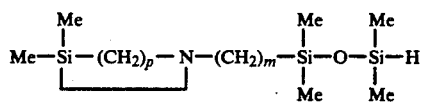

in which Me is methyl, m has a value of 3 to 6 inclusive, and p has a value of 4 to 6 inclusive.

13. An azasilacyclalkyl functional tetramethyldisiloxane of the formula

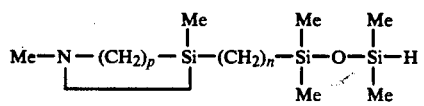

in which Me is methyl, n has a value of 2 to 6 inclusive, and p has a value of 4 to 6 inclusive.

* * * * *